United States Patent
Sriyudthsak et al.

(10) Patent No.: US 9,452,428 B2
(45) Date of Patent: Sep. 27, 2016

(54) METHOD OF MAKING A MICROFLUIDIC DEVICE

(71) Applicant: National Science and Technology Development Agency, Klong Luang Pathumthani (TH)

(72) Inventors: Mana Sriyudthsak, Nonthaburi (TH); Apinan Soottitantawat, Tavewatna Bangkok (TH); Yongyuth Wanna, Pathumthan (TH); Sakon Rahong, Changmai (TH); Vichuta Lauruengtana, Pathumthani (TH); Naoki Ichikawa, Ibaraki (JP); Sohei Matsumoto, Ibaraki (JP); Ryutaro Maeda, Tsuchiura (JP)

(73) Assignee: National Science and Technology Development Agency, Pathumthani (TH)

(*) Notice: Subject to any disclaimer, the term of this patent is extended or adjusted under 35 U.S.C. 154(b) by 153 days.

(21) Appl. No.: 14/534,502

(22) Filed: Nov. 6, 2014

(65) Prior Publication Data

US 2015/0064688 A1   Mar. 5, 2015

Related U.S. Application Data

(62) Division of application No. 12/131,627, filed on Jun. 2, 2008, now abandoned.

(30) Foreign Application Priority Data

May 31, 2007 (JP) .................................. 2007-145346

(51) Int. Cl.
*B01L 3/00* (2006.01)
*C12Q 1/25* (2006.01)

(52) U.S. Cl.
CPC ........ *B01L 3/502707* (2013.01); *B01L 3/5027* (2013.01); *C12Q 1/25* (2013.01); *B01L 2200/10* (2013.01); *B01L 2300/0636* (2013.01); *B01L 2300/0645* (2013.01); *B01L 2300/0663* (2013.01); *B01L 2300/0816* (2013.01); *B01L 2300/0887* (2013.01)

(58) Field of Classification Search
CPC .................. B01L 2200/10; B01L 2300/0636; B01L 2300/0645; B01L 2300/0663; B01L 2300/0816; B01L 2300/0887; B01L 3/5027; B01L 3/502707; C12Q 1/25
USPC ............................................... 156/245; 435/4
See application file for complete search history.

(56) References Cited

U.S. PATENT DOCUMENTS

| | | | |
|---|---|---|---|
| 5,225,321 | A | 7/1993 | Hayashi et al. |
| 2004/0121356 | A1 | 6/2004 | Yamagata et al. |
| 2005/0014175 | A1 | 1/2005 | Quake |

FOREIGN PATENT DOCUMENTS

| | | | |
|---|---|---|---|
| JP | 2002283293 A | 10/2002 | |
| JP | 2004167607 A | 6/2004 | |
| JP | 2004194652 A | 7/2004 | |

*Primary Examiner* — Dirk Bass
(74) *Attorney, Agent, or Firm* — Dorsey & Whitney LLP

(57) ABSTRACT

A microfluidic device allowing for multiple discrete reactions sites and allowing for sequential reactions and sample analysis along with methods for device fabrication and use is provided. The microfluidic device provides a micro-total analysis system on a single substrate and has multiple reaction sites allowing for cascade reactions and analysis on a single chip using micro-quantities of sample and reagents. The microfluidic device provides discrete sites for immobilization of cognitive agents including enzymes, binding proteins, nucleic acids and the like as well as methods for quantitative analysis. The invention also provides methods for the fabrication of the device.

11 Claims, 3 Drawing Sheets

METHOD OF MAKING A MICROFLUIDIC DEVICE

CROSS-REFERENCE TO RELATED APPLICATION

This application is a divisional of U.S. Ser. No. 12/131,627 filed Jun. 2, 2008, which claims priority to Japanese patent application number 2007-145346 filed May 31, 2007 both of which are herein incorporated in their entirety.

FIELD OF THE INVENTION

This invention relates to a microfluidic device for use with a micro-total analysis system (µ-TAS) having discrete areas with multiple cognitive agents immobilized thereon. More specifically, the invention provides a lab-on-a-chip device that allows for cascade or sequential reactions and product analysis on a micro-scale.

BACKGROUND OF THE INVENTION

Chemical component analysis is extensively used in many and varied fields. However, the uses for such chemical component analysis have been limited due the requirement for special equipment, physical space for the equipment, and the amount of time necessary for preparing for and conducting the analysis. To address these problems, there is much interest in developing "micro-total analysis systems" (µ-TAS) having dimensions similar to a credit card. Such systems combine a separating device, mixing device, measuring device, and analyzing device on the same substrate. Ideally, in use, the µ-TAS can deliver the sample solution to the analysis equipment and then analyze the sample while requiring microliters of sample at most. Moreover, the µ-TAS can be operated using similarly small amounts of reagents. Such systems have uniform reaction temperatures, superior controllability, and are disposable improving safety and hygiene.

Analysis by µ-TAS is useful in a number of applications including, but not limited to, medical, industrial, agriculture, molecular, and forensic investigations. Examples of medical applications include but are not limited to, measurement and inspection of blood components and biochemical analysis, such as measurement and inspection of various types of proteins, hormones, and antibodies. Examples industrial applications include but are not limited to, component analysis in manufactured products, component analysis of waste-water and component analysis of raw materials. Examples of use in agriculture include but are not limited to, measurement of sugar content in vegetables and fruits and measurement of chemical/pesticide residues both in the environment and on produce. Examples for use with genetic analysis include but are not limited to decoding of genetic information for diagnosis and prevention of genetic diseases.

For chemical component analysis in solution, µ-TAS employs microfluidic devices in which an internal channel is immobilized with a cognitive agent, such as, for example, an enzyme for a reaction catalyst or antibodies, binding proteins and receptors for capturing desired substrates or analytes. Such cognitive agents can be used to react specifically with a desired analyte (detected substance). Currently, microfluidic devices using the above mentioned cognitive agents such as enzymes, antibodies, binding proteins, etc. are limited because only a single cognitive agent is immobilized in the channels of the microfluidic device. When used in chemical component analysis in solution and for which multiple cognitive agents, e.g. enzymes or antibodies, receptors, ligands or the like are used, the solution sample has to be multiply contacted and reacted with different and multiple immobilized cognitive agents. This requires several microfluidic devices immobilized with single cognitive agent, as mentioned above, that are linked by a connecting channel of each device to form a composite device; or by connecting the microfluidic devices and connecting the channels. The deficiencies of these approaches are the difficulty of use and maintenance, solution leak at the joints which requires substantially reinforced joint areas, increases space needs and larger amounts of sample and reagent. These deficiencies result in a large amount of time needed in constructing and connoting the various devices, large amount of time needed to perform the analysis as well as more costly devices cost of analysis time and less consistent results.

Several methods of fabricating micro channel devices. These include, methods of forming a resin layer on a substrate (JP nos. 2002-283293 and 2004-167607) by attaching a resin layer formed by laser on a silicon, glass, or ceramic substrate; methods of fabricating a channel using a photoresist and exposing it to ultraviolet light through a mask, then removing non-exposed parts (JP no. 2004-194652); methods of fabricating a channel by micro-discharge; and methods of mechanical fabrication (etching) using a hard material, e.g. diamond, as a tool for the micro-fabrication. Additionally, methods of micro-channel fabrication using a mould begins with coating the photoresist on silicon substrate, exposing it through a mask, and removing the photoresist to generate an embossed portion to form a mould for the micro-channel on silicone substrate, adding a mixture of polydimethyl siloxane (PDMS) and hardening material onto the mould, obtaining a groove of the channel as the mixture hardens, detaching the hardened layer off the mould, and attaching the hardened layer on a substrate, e.g. silicone or glass (JP no. 2004-296099).

As with methods of fabricating microfluidic devices, methods of immobilizing enzymes can also be performed in various ways. However, a method of immobilizing different cognitive agents, such as multiple enzymes or antibodies, onto a single channel in discrete positions for use in continuous or cascade reactions is not known. Currently, a screen printing technique can be used for immobilizing different enzymes onto the same substrate, but the accuracy of placement is limited to a range of 500 µm to 1 mm. This limitation is far in excess of what is required for µ-TAS analysis.

In instances of reactions such as catalytic reactions, binding reactions, or antigen-antibody reactions, that include multiple steps that need to be performed continuously or sequentially using multiple cognitive agents, e.g. enzymes, antibodies; the use of a microfluidic device in these instances should be capable of controlling the reaction, using only minimal amounts of reactants/reagents as well as providing high efficiency. Furthermore, in cases of cascade reactions occurring in a single micro-channel it is a necessity to provide controlled and reproducible environment. For example, in a small system, it is difficult to separate the $1^{st}$ reaction zone, from the $2^{nd}$ reaction zone. But, if one were capable of immobilizing different cognitive agents at different positions along the micro-channel, the product from the $1^{st}$ reaction could be used in the $2^{nd}$ reaction and so on. To achieve such cascade reactions, it is necessary to immobilize the cognitive agents in different positions along the channel path in a discrete and well-defined manner. At present, it is difficult to immobilize cognitive agents in different positions along a micro-channel path having a uniform channel width with accuracy better than 500 μm. However, the use of narrower channels would result less reagents used and also provide more consistent results, reproducible reaction in much less time.

Therefore, it is desirable to provide a microfluidic device having different cognitive agents immobilized in discrete positions along a micro-scale channel that would allow sequentially reaction to be performed thereon. In some instances, it would be further desirable to utilize a method of quantitative component analysis to analyze the results.

SUMMARY OF THE INVENTION

A microfluidic device allowing for multiple discrete reactions sites and allowing for sequential reactions and sample analysis along with methods for device fabrication and use is provided. The microfluidic device provides a micro-total analysis system on a single substrate and has multiple reaction sites allowing for cascade reactions and analysis on a single chip using micro-quantities of sample and reagents. The microfluidic device provides discrete sites for immobilization of cognitive agents including enzymes, binding proteins, nucleic acids and the like as well as methods for quantitative analysis. The invention also provides methods for the fabrication of the device.

Accordingly, in one exemplary embodiment, the invention provides a microfluidic device comprising a reaction channel fabricated from a reaction layer on a substrate, including at least two reaction channel networks, wherein the at least two reaction channel networks are immobilized with at least one cognitive agent allowing for a sequential reaction along the reaction channel. In various exemplary embodiments, the cognitive agent is selected from enzymes, antigens, antibodies, proteins, receptors, ligands, nucleic acids or combinations thereof. In some exemplary embodiments, the at least two reaction channel networks have different cognitive agents immobilized thereon. In various other embodiments according to the invention, the reaction layer is made from glass, silicone, polydimethyl siloxane, other silicone resins, polymethyl methacrylate (PMMA), synthetic acrylic, or polycarbonate. In various exemplary embodiments, the substrate is made from glass, silicone, polyvinyl chloride, polyester, polyimide, acrylic resin, polycarbonate, cellulose acetate, polyacrylic amide, or polyacrylonitrile. In various exemplary embodiments, the substrate has a sensor measurement. In some exemplary embodiments, the sensor is an electrode, an optical sensor, a thermal sensor, or a chemosensor.

In still other exemplary embodiments, the invention includes a method of fabrication of a microfluidic device having discrete regions of cognitive agents immobilized thereon comprising the steps of providing a substrate, attaching an immobilization layer having one or more channel networks formed therein to the substrate; flowing one or more solution of cognitive agents into the channel networks; immobilizing one or more cognitive agents onto the substrate surface at the one or more channel networks; detaching the immobilization layer from the substrate; positioning a reaction layer including a single reaction channel to the substrate and wherein the single reaction channel encompasses the one or more channel networks. In some exemplary embodiments, the solution of cognitive agents is an enzyme solution, an antigen solution, an antibody solution, a protein solution, a receptor solution, a ligand solution, a nucleic acid solution or combinations thereof. In still other exemplary embodiments, the method includes a step of substrate surface pre-treatment, prior to the step of attaching the immobilization layer. In some embodiments according to the invention, the pre-treatment step is performed prior to flowing the cognitive agent solution through the channel network. In various exemplary embodiments the pre-treatment step comprises deposition of a gold layer.

In yet another, exemplary embodiment, the invention comprises a step of introducing a solution to be analyzed into the reaction channel of the microfluidic device according to the invention and allowing a component in the solution to flow through the at least two reaction channel networks with the one or more cognitive agents in sequence, and measuring an amount of reaction product.

These and other features and advantages of the present invention will be set forth or will become more fully apparent in the description that follows and in the appended claims. The features and advantages may be realized and obtained by means of the instruments and combinations particularly pointed out in the appended claims. Furthermore, the features and advantages of the invention may be learned by the practice of the invention or will be apparent from the description, as set forth hereinafter.

BRIEF DESCRIPTION OF THE FIGURES

Various exemplary embodiments of the compositions and methods according to the invention will be described in detail, with reference to the following figures wherein.

DETAILED DESCRIPTION OF THE EXEMPLARY EMBODIMENTS

Figure 1:
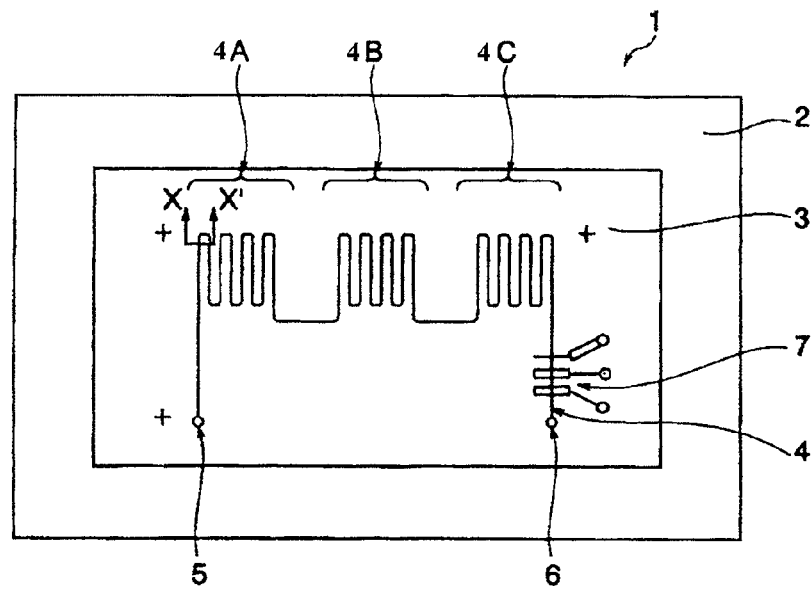
FIG. 1 illustrates a top view of the microfluidic device according to this invention.

A microfluidic device allowing for multiple discrete reactions sites and allowing for sequential reactions and sample analysis along with methods for device fabrication and use is provided. The microfluidic device provides a micro-total analysis system on a single substrate and has multiple reaction sites allowing for cascade reactions and analysis on a single chip using micro-quantities of sample and reagents. The microfluidic device provides discrete sites for immobilization of cognitive agents including enzymes, binding proteins, nucleic acids and the like as well as methods for quantitative analysis. The invention also provides methods for the fabrication of the device.

Accordingly, in one exemplary embodiment, the invention provides a microfluidic device comprising a reaction channel fabricated from a reaction layer on a substrate, including at least two reaction channel networks, wherein the at least two reaction channel networks are immobilized with at least one cognitive agent allowing for a sequential reaction along the reaction channel. In various exemplary embodiments, the cognitive agent is selected from enzymes, antigens, antibodies, proteins, receptors, ligands, nucleic acids or combinations thereof. In some exemplary embodiments, the at least two reaction channel networks have different cognitive agents immobilized thereon. In various other embodiments according to the invention, the reaction layer is made from glass, silicone, polydimethyl siloxane, other silicone resins, polymethyl methacrylate (PMMA), synthetic acrylic, or polycarbonate. a polymer. In various exemplary embodiments, the polymer includes plastics polydimethyl siloxane, polycarbonate, acrylic resin, polyvinyl chloride, polyacrylic amide or polyacrylonitrile. In some exemplary embodiments, the substrate is made from glass, silicone, polyvinyl chloride, polyester, polyimide, acrylic resin, polycarbonate, cellulose acetate, polyacrylic amide, or polyacrylonitrile. In various exemplary embodiments, the substrate has a sensor measurement. In some exemplary embodiments, the sensor is an electrode, an optical sensor, a thermal sensor, or a chemosensor.

In still other exemplary embodiments, the invention includes a method of fabrication of a microfluidic device having discrete regions of cognitive agents immobilized thereon comprising the steps of providing a substrate, attaching an immobilization layer having one or more channel networks formed therein to the substrate; flowing one or more solution of cognitive agents into the channel networks; immobilizing one or more cognitive agents onto the substrate surface at the one or more channel networks; detaching the immobilization layer from the substrate; positioning a reaction layer including a single reaction channel to the substrate and wherein the single reaction channel encompasses the one or more channel networks. In some exemplary embodiments, the solution of cognitive agents is an enzyme solution, an antigen solution, an antibody solution, a protein solution, a receptor solution, a ligand solution, a nucleic acid solution or combinations thereof. In still other exemplary embodiments, the method includes a step of substrate surface pre-treatment, prior to the step of attaching the immobilization layer. In some embodiments according to the invention, the pre-treatment step is performed prior to flowing the cognitive agent solution through the channel network. In various exemplary embodiments the pre-treatment step comprises deposition of a gold layer.

In yet another, exemplary embodiment, the invention comprises a step of introducing a solution to be analyzed into the reaction channel of the microfluidic device according to the invention and allowing a component in the solution to flow through the at least two reaction channel networks with the one or more cognitive agents in sequence, and measuring an amount of reaction product.

Before the present methods are described, it is understood that this invention is not limited to the particular methodology, protocols, cell lines, and reagents described, as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "a cell" includes a plurality of such cells and equivalents thereof known to those skilled in the art, and so forth. As well, the terms "a" (or "an"), "one or more" and "at least one" can be used interchangeably herein. It is also to be noted that the terms "comprising", "including", and "having" can be used interchangeably.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference for the purpose of describing and disclosing the chemicals, cell lines, vectors, animals, instruments, statistical analysis and methodologies which are reported in the publications which might be used in connection with the invention. Nothing herein is to be construed as an admission that the invention is not entitled to antedate such disclosure by virtue of prior invention.

As used herein, the term "sensor" refers to any a device which measures a physical quantity and converts it into a signal which can be read by an observer or by an instrument. For example, an "optical sensor" as used herein is a sensing device that measures changes in ultraviolet light (UV), infrared light (IR), visible light, fluorescence, luminescence and the like. Further, those of skill in the art will recognize that such sensors are well known and may measure both the amount of light absorbed by a compound or analyte, the amount of light reflected or the amount of light emitted. A temperature sensor can be as simple as a thermometer which simply allows visualization of the contraction and expansion of mercury in a closed tube or a thermocouple which converts temperature to an output voltage that is read by a voltmeter. Briefly, sensors include thermal sensors, electromagnetic sensors, mechanical sensors, chemical sensors, optical sensors, ionizing radiation sensors and acoustic sensors. Examples of chemical sensors include Chemical proportion sensors: oxygen sensors, ion-selective electrodes, redox electrodes, and carbon monoxide detectors. Odor sensors: Tin-oxide gas sensors, and Quartz Microbalance sensors. An ion selective electrode is a transducer which converts the activity of a specific ion dissolved in a solution into an electrical potential which can be measured by a voltmeter or pH meter. Such ion selective electrodes may be as simple as a glass pH electrode that responds to single charged ions such as $H^+$, $Na^+$, and $Ag^+$. However there are more complex electrodes available such as those that measure divalent metal ions, such as $Pb^{2+}$ and those that measure redox potential etc.

As used herein the term "cognitive agent" means any molecule capable of specific attraction another molecule. Cognitive agents can be antibodies or fragments of antibodies that have binding domains such as Fab's or partial Fab's. Capture molecules can be "ligands" or "receptors" either partial or complete and whether or not they are associated with other molecules or compounds. As used herein the term "ligand" refers a molecule that binds to another molecule. Generally, a ligand may be soluble and its binding partner is referred to as a "receptor". Unless otherwise defined, receptors are generally regarded as being associated with particular cells. Classically, receptors transduce a signal conferred by a ligand with the binding of the ligand to the receptor resulting in a signal to the cell and a physiologic response. Receptors may be on the cell surface on within the cells. As a rule, peptide or protein hormones are ligands that bind to receptors at the cell surface while steroid hormones are ligands that pass through the cell membrane and bind to receptors in the cell nucleus. Receptors can become soluble and act as a ligand. Thus, the terminology of "receptor" and "ligand" may become interchangeable. Generally, a receptor is thought to be larger than its cognate ligand.

As used herein, the term "substrate" is used to refer to the support layer of the microfluidic device. As such, the substrate may be any material as long as it is strong enough to support the overlying reaction layer and fabrication steps and also does not interfere with or react with the components of the analysis. Such substrates can include, but are not limited to, glass, silicone, and polymers including generally plastics such as, for example polyvinyl chloride, polyester, polyimide, acrylic resin, polycarbonate, cellulose acetate, polyacrylic amide, and polyacrylonitrile.

Figure 2:
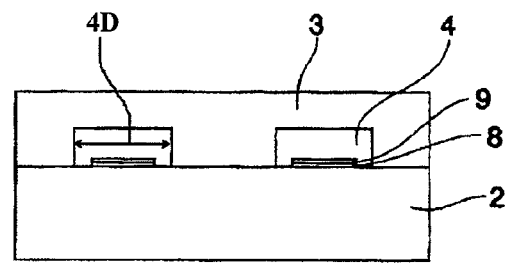
FIG. 2 illustrates a cross section along X-X' of the microfluidic device in FIG. 1.

A detailed description of the embodiment of invention is shown as follows:

Referring now to FIGS. 1 and 2, one exemplary embodiment of a microfluidic device according to the invention is shown. FIG. 1 is a top-plan view of a microfluidic device according to the invention. FIG. 2 is a cross-section of the exemplary embodiment of the invention shown in FIG. 1 taken along X-X'. As illustrated, the device 1 comprises a substrate 2 which includes a reaction layer 3, a reaction channel 4 formed thereon, an inlet 5, an outlet 6 and a sensor 7 for measurement such as for example, an electrode, a thermal sensor, an optical sensor or a chemosensor such as are well known to those of skill in the art. FIG. 2, further illustrates a pre-treatment membrane 8 for cognitive agent immobilization, and a cognitive agent 9 such as, for example, an enzyme, an antibody, a protein or a receptor, immobilized thereon. FIG. 2 further shows that the reaction layer 3 has a reaction channel or groove 4 formed therein, the reaction layer 3 overlaying the substrate 2. Within the channel 4, is a pre-treatment membrane 8 which assists in the immobilization of cognitive agents 9.

Also shown in FIG. 1, the reaction channel 4 includes an inlet 5 and an outlet 6. Thus, generally a solution to be analyzed is entered into the device at the inlet and exits at the outlet. The channel can be divided in three reaction channel network—sections 4A, 4B, and 4C which, in some exemplary embodiments comprise multiple folded reaction channels. In the exemplary embodiment illustrated, each reaction network section can be immobilized with the different cognitive agents. An electrode 7, according to one exemplary embodiment of a sensor is used for measuring components or analytes in a sample and, in some embodiments provided on the substrate.

As disclosed herein, the substrate 2 is made from any material, which does not react with components in the sample solution and is not detrimental to the cognitive agent/s immobilized thereon. For example, the substrate can be made from inorganic materials, e.g. glass and silicone; or organic materials such as synthetic resins, e.g. polyvinyl chloride, polyester, polyimide, acrylic resin, polycarbonate, cellulose acetate, polyacrylic amide, polyacrylonitrile, etc. Because most sample solutions use water as a solvent, it is desirable to use a synthetic resin, which has hydrophilic property. However, in embodiments in which a hydrophobic material is used as a substrate, surface modification or surface coating with a hydrophilic material may be required to improve the hydrophilicity. Generally, there is no particular requirement for the substrate thickness. However, it will be appreciated the substrate provides adequate strength and flexibility so as not to allow the solution to leak from the surrounding channel. Obviously, in those instances where the solvent is not water, the substrate may be chosen accordingly and surface modification may not be necessary Materials useful for forming the reaction layer 3 will be recognized by those of skill in the art. Generally, such materials should have similar properties to the substrate, which are hydrophilic materials, and also should not react with sample constituents and/or products from the sample reaction, nor be harmful to the cognitive agent. Further, according to one exemplary embodiment, because the reaction layer is attached to the substrate which has a cognitive agent immobilized thereon, the material of the reaction layer 3 should adhere well to the substrate, at least transiently during the time of the analysis. Further, the reaction layer should be amenable to forming a small groove therein thus providing the channel for the solution to flow through. However, those of skill in the art will recognize that the channel can also be formed in the substrate 2, layer. Examples of materials useful for forming the reaction layer include polydimethyl siloxane (PDMS), which is a silicone resin material. However, in this invention, the materials for forming the channel layer can include any materials with stated properties, such as PDMS and other silicone resins. Alternatively, other materials, can be used so long as they are capable of bonding to the substrate surface by any acceptable bonding or adhesive material so long as there is no leakage of the sample entered therein. Examples of material used as the channel layer are inorganic materials, e.g. glass, silicone; or well-known synthetic resins, e.g. poly methyl methacrylate (PMMA), synthetic acrylic, polycarbonate, etc.

As shown in FIG. 1, the channel 4 has one or more network portions (4A, 4B, 4C) each have a width 4D. The network sections provide increased length and therefore increased surface area and reaction time for the sample in solution to react with the cognitive agent. FIG. 1, illustrates one exemplary embodiment wherein the network sections 4A, 4B, or 4C of the reaction channel 4 increases the surface area on which the cognitive agent is immobilized and contacts the sample solution. However, it should be appreciated that if less reaction time is needed the network portion can be shortened or omitted altogether, i.e. the network portion can have a short, straight line profile. Further, while as illustrated in the exemplary embodiment shown in FIG. 1, the three network sections 4A, 4B and 4C all have the same length for the reaction channel network on which cognitive agents are immobilized, those of skill in the art will appreciate that the length of channel for each portion may be different according to the component to be analyzed and measured or the cognitive agent to be immobilized therein. Thus, the length of the channel for each cognitive agent or reaction mixture used in each section can differ and may be optimized as needed.

In various exemplary embodiments according to the invention, several cognitive agents can be immobilized on the substrate in different positions along the channel path as needed. In FIG. 1, the channel provides reaction network sections 4A, 4B and 4C allowing for the immobilization of three different cognitive agents along the reaction network section of the reaction channel. In practice, the number of cognitive agents may only be one or greater than three. The number and type of cognitive agents can be changed depending on the solution/compounds to be analyzed. The cognitive agent may be an enzyme which functions in a catalytic reaction, but cognitive agents are not limited to enzymes. For example, other materials which specifically recognize the measured chemical substance can be antigens, antibodies, proteins, receptors, or nucleic acids including DNA, RNA and PNA. Further, examples of enzymes used as cognitive agents include but are not limited to, invertase, mutarotase, glucose oxidase, alcohol oxidase, lacto oxidase, amino acid oxidase, catalase, uricase, cholesterol oxidase, hexokinase, urease, trypsin, etc. Of course other enzymes can also be used with the microfluidic device in accordance with the invention. Since various cognitive agents are immobilized on this device, the types and sequences of cognitive agents can also be altered or optimized for analysis of each analyzed component. For example, when the invention is used to analyze the sweetness of fruits or sugar cane, one suitable fixing sequence useful is invertase in section A, mutarotase in section B, and glucose oxidase in section C.

As mentioned above, in some instances it may be difficult to immobilize the cognitive agent on the substrate directly. Hence, prior to the cognitive agent immobilization, surface modification of the substrate may be made by providing a pre-treatment or a fixation of an immobilization reagent. In these instances a pre-treatment layer 8 may be applied. For example, any conventional pre-treatment method generally used for cognitive agent immobilization on a substrate of may be employed. Examples of pre-treatment methods for immobilization of the enzyme include vacuum evaporation of silver, gold, or platinum or flowing a solution of an osmium polymer. However, it should be appreciated that the method of pre-treatment in this invention is not limited to the examples provided herein. Further, in the case of gold coating by evaporation, it may be necessary to apply a chromium or titanium layer before applying the gold layer to improve adhesion on the glass substrate. In case of the osmium polymer, an osmium polymer solution can be used. Of course, other materials can be used as a pre-treatment layer too. Further, the chemical substance for the immobilization may be flowed concurrently with the solution of cognitive agent during the immobilization. One example of a chemical substance useful for enzyme immobilization is glutaraldehyde. In such cases, the coating of pre-treatment layer 8 is not required for the cognitive agent to be immobilized directly on the substrate. Thus, in instances, the cognitive agent can immobilized directly on the substrate, and the pre-treatment layer is not necessary.

Fabrication of the Microfluidic Device

Figure 3:
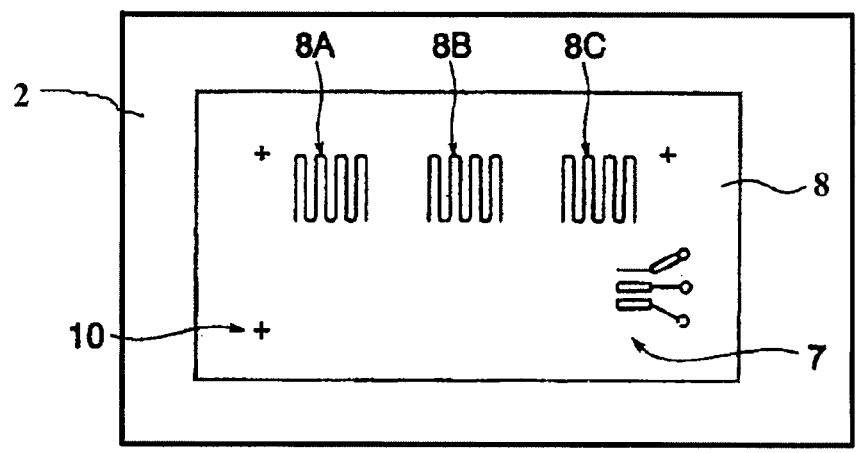
FIG. 3 illustrates a top view of the substrate coated with a pre-treatment membrane for cognitive agent immobilization.
Figure 4A:
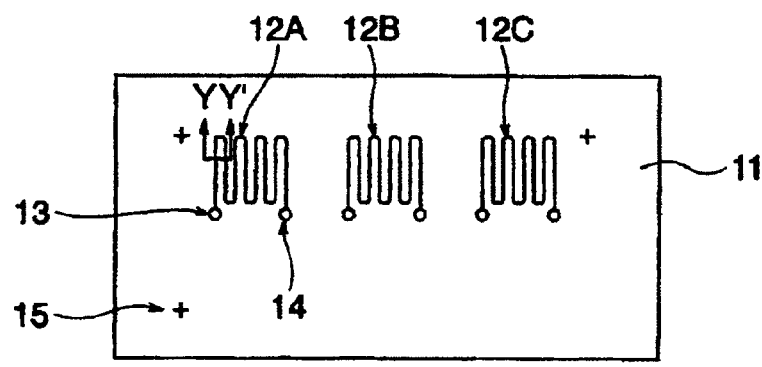
FIG. 4a illustrates a top view of the immobilization layer for cognitive agent immobilization.
Figure 4B:
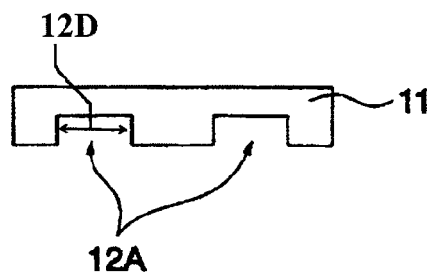
FIG. 4b illustrates a cross section along Y-Y' of the device in FIG. 4(a).
Figure 5:
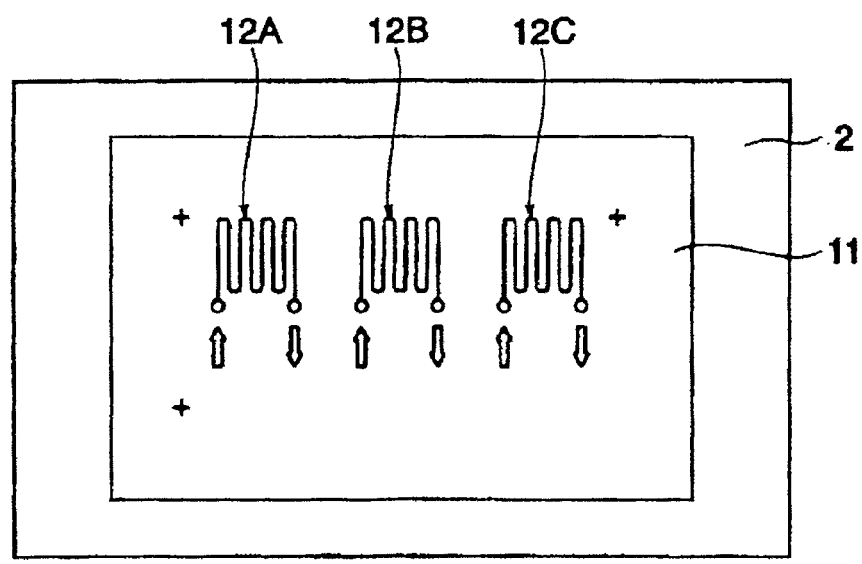
FIG. 5 illustrates a top view of the substrate with the immobilization layer including the network channels for the cognitive agent immobilization attached thereto.

In another embodiment, the invention provides a method of fabricating a microfluidic device according to the invention. FIG. 3 illustrates a top view of the substrate coated with a pre-treatment layer prior to cognitive agent immobilization. FIG. 4(a) illustrates a top-plan view of the immobilization layer 11 used for the cognitive agent immobilization. FIG. 4(b) illustrates a cross-section along Y-Y' shown in FIG. 4(a). FIG. 5 is a top-plan view of the substrate with the immobilization layer 11 attached for cognitive agent immobilization.

As shown in FIG. 3, pre-treatment membrane 8 includes channel network sections 8A, 8B, and 8C. It should be noted that in some exemplary embodiments, the pre-treatment channel width may be smaller (8D not shown) than the width 4D of the reaction channel. The pre-treatment network sections 8A, 8B and 8C are formed as a line pattern at three discrete locations corresponding to the reaction channel path 4 on the substrate 2. In FIG. 3, the pre-treatment networks are formed at three discrete locations. However, as mentioned above, if only two cognitive agents are needed, then only two pre-treatment network sections at two locations will be necessary etc. But if more than four cognitive agents are needed, more than four pre-treatment networks will be used. As discussed above, if the cognitive agent can be immobilized directly on the substrate, it is not necessary to modify the substrate surface using a pre-treatment layer. However, in those instances when the cognitive agent is an enzyme, antibody, nucleic acid, binding protein or receptor, etc., it is difficult to immobilize the agent directly on the substrate. In addition, it should be appreciated that each network section may have different cognitive agents immobilized thereon and that therefore, each pre-treatment network section may be optimized for the specific cognitive agent to be immobilized thereon. In addition, in most cases the substrate pre-treatment will be performed prior to immobilization of the cognitive agent onto the substrate. Of course, any known pre-treatment method useful for cognitive agent immobilization can be used.

For example, a method for the deposition of a gold layer using evaporation is one example of a pre-treatment method useful for cognitive agent immobilization. One method of forming a gold evaporated layer as a fine line pattern onto the substrate can be conducted by coating a photoresist or attaching a photosensitive dry film onto the substrate, exposing light through a mask with the line pattern, and developing the film to form a photoresist layer with a network channel line on the substrate, then evaporating the gold layer, and removing the photoresist to form the desired pattern for the reaction channel network. An alternative method is evaporating the gold on an entire surface of the substrate, coating the photoresist onto the gold layer, exposing light through a mask with the network pattern, and developing the photoresist to form with a network pattern on the substrate, then etching the gold that does not have the photoresist. Another method is a direct evaporation of the gold through a stencil mask having apertures facilitating evaporation where the stencil is attached to the substrate. In the case of forming a gold evaporation layer as the pre-treatment layer, it may be formed, if necessary, simultaneously with the forming of the sensor 7 which is used as a measuring device. The sensor used as the measuring device may be formed in advance on the substrate. Furthermore, the alignment marker 10 can be prepared in the same step, and certainly the alignment marker 10 can be prepared in advance on the substrate.

Next, as shown in FIG. 4, to immobilize the cognitive agent, such as, for example, an enzyme, an immobilization layer 11 is used for cognitive agent immobilization. The immobilization layer 11 has networks or grooves 12A, 12B, 12C corresponding to the reaction channel network 4A, 4B and 4C and pre-treatment channel network 8A, 8B and 8C and is attached onto the substrate so as to align with the pre-treatment networks or grooves formed by the pre-treatment layer. The immobilization layer 11 contains a channel networks as necessary, for cognitive agent immobilization and is attached on the substrate 2 as shown in FIGS. 4 and 5. As with the pre-treatment layer, the channel networks have a width 12D that, in exemplary embodiments is about the same or less than the width 4D of the reaction channel networks 4A, 4B and 4C. The immobilization layer 11 is generally detachably fixed to the substrate to prevent leakage of the cognitive agent solution from the immobilization channel network during flow of the cognitive agent solution through the channel. Hence, the immobilization layer 11 for the cognitive agent immobilization should have excellent adhesion but also be easy to detach. In most cases adhesives or coupling agents are not easily detachable.

Therefore, some exemplary embodiments, the immobilization layer 11 for the cognitive agent immobilization is not attached to the substrate use adhesives or bonding agents. However, it should be appreciated that in those cases where adhesives or bonding agents used are detachable, and also do not allow leakage from the channel, their use during cognitive agent immobilization is contemplated by the invention. In these cases, it is possible to use an adhesive that allows the immobilization layer to be detached from the substrate. Hence, it is possible to use an inorganic material, e.g. glass and silicon; general casting materials, e.g. polycarbonate, acrylic resin as the substrate. Polydimethyl siloxane (PDMS) is an example of material having excellent adhesion and is easy to remove from the above mentioned substrates. One method of forming a channel or groove in polydimethyl siloxane useful for flowing a cognitive agent solution along the pre-treatment network is to first, prepare the photoresist layer on the substrate, e.g. glass, with the same thickness as the pre-treatment network, exposing UV light through a patterned mask having the network pattern of the pre-treatment layer, developing the photoresist layer having the same or slightly greater width than the pre-treatment layer. The result is a photoresist layer that is used as a mould. Next, a mixture of polydimethyl siloxane solution and hardener is poured into the mould and cured providing the polydimethyl siloxane layer with the multiple network channels comprising the network pattern of the pre-treatment layer. The obtained immobilization layer is removed from the mould, and then apertures comprising an inlet 13 and outlet 14 are created using a suitable device such as a needle, scalpel etc. providing an immobilization channel network 12A, 12B and 12C with width 12D in the immobilization layer 11 suitable for cognitive agent 9 immobilization. In some exemplary embodiments, an alignment marker 15 is also formed in the immobilization layer 11 to help align the position of the immobilization layer 11 on the substrate 2. Hence, it is suitable to prepare the alignment marker on the mould, for copying and forming a replica of the reaction layer and providing a channel for cognitive agent immobilization.

As described herein a solution of different cognitive agents can flow from the inlet 13 to the outlet 14 of each immobilization network section 12A, 12B, 12C formed by the immobilization layer 11 and allowing for cognitive agent 9 immobilization for each network section 12A, 12B or 12C or other region of the channel 4 as desired. In some exemplary embodiments, to facilitate the solution flow, the outlet pressure is reduced, such as, for example, by use of a vacuum or suction. In addition, decreasing the outlet pressure, can be useful in preventing the immobilization layer 11 from detaching from the substrate 2 during cognitive agent immobilization. For example, a tube can be used as a connection to prevent the solution containing the cognitive agent from leaking at the inlet 13 and outlet 14, and to facilitate the flow of the desired cognitive agent for each of the immobilization networks of the channel. Using the tube at the outlet 14 also facilitates a reduction of outlet pressure and ease of collection of used solution. Further, the inlet and outlet positions can be exchanged if it is helpful to apply the cognitive agent solution from either or both ends of the immobilization network. For example, in the case of using enzyme mutarotase as a cognitive agent, a commercial mutarotase solution is passed into the inlet, then the pressure at the outlet is reduced, a hazy solution can be observed in the interior of channel within about a minute. Furthermore, in cases where the interior of the channel is pre-treated to be hydrophilic to assist the solution flow, the solution will flow easily providing contact with the channel within about a minute. The effluent solution is then collected and the interior of the channel is allowed to dry. After detaching the immobilization layer 11 used for cognitive agent immobilization, the substrate 2 immobilized with the cognitive agent/s is obtained.

The reaction layer 3 is then attached onto the substrate 2 immobilized with the cognitive agent thereby providing the microfluidic device as shown in FIG. 1. Polydimethyl siloxane (PDMS) is one of suitable materials for forming reaction layer 3, however; other materials can be applied too. In case of using polydimethyl siloxane as the material for the reaction layer 3, it can also be prepared in the same method as the one for forming the immobilization layer 11. In some instances, the channel width 4D of the reaction channel 4 should be about the same or slightly greater than the channel width 12D of immobilization channel networks 12A, 12B, 12C. In these cases, the reaction channel 4 or groove width of the reaction layer 3 should be larger than the channel width of the immobilization layer channel 12A.

Additionally, the method of forming the channels or grooves 12A, 12B, 12C of the immobilization layer 11 or the channels or grooves of the reaction network sections 4A, 4B and 4C of the reaction layer 3 are not limited to aforementioned ones. Other methods compatible with the material used can be exploited, for example, such methods include but are not limited to forming the channels by laser or photoresist.

The microfluidic device according to this invention can be used for component analysis or inspection various solutions. An example of component analysis is a measurement of sucrose concentration in fruits or sugar cane. In this case, the invention can be used by the immobilization of invertase, mutarotase, and glucose oxidase enzymes at the reaction channel networks in sections 4A, 4B and 4C respectively. A juice squeezed from sugar cane is dropped at a volume of as low as about 2-5 µl into inlet 5 of the microfluidic device 1, reducing the outlet 6 pressure and facilitating the solution flow into the reaction channel 4. When the solution flows along network section 4A, the sucrose is converted to α-D glucose and fructose by a hydrolysis reaction catalyzed by invertase; in section 4B, α-D glucose is converted to β-D glucose catalyzed by mutarotase; and then into section 4C, where β-D glucose converting to hydrogen peroxide and glucuronic acid catalyzed by glucose oxidase. Then, at the sensor, an electrode 7 measures an amount of hydrogen peroxide as to determine the sucrose concentration in of the plant extract.

Of course, those of skill in the art will recognize that other methods for the measurement of analyte concentration or other compounds in solution, can be used besides measurement of electrical conductivity. For example, such methods known in the art include changes in optical parameters, thermal parameters and frequency changes of piezoelectric devices, etc. Specific methods of measurement include, but are not limited to the measurement of optical luminescence including chemiluminescence of an enzyme-immunoassay, the measurement of light absorption and emitted fluorescence to name a few.

EXAMPLES

Various exemplary embodiments of the devices, compounds and methods as generally described above according to this invention, will be understood more readily by reference to the following examples, which are provided by way of illustration and are not intended to be limiting of the invention in any fashion.

Example 1

Pretreatment of the Substrate

As described above, a first step in the fabrication of the device is the pretreatment of the substrate surface. Referring now to FIG. 3, three sets of evaporated gold layers are shown at 8A, 8B and 8C. In the embodiments shown, each of the gold layers has a four-part network portion having 100

μm width which were fabricated on a glass substrate using the photolithography technique described above.

Briefly, the substrate is prepared by cleaning with a solvent such as acetone or methylene chloride and allowed to dry. Substrate surface modification with a pre-treatment layer was made by using a SU-8 thick film photoresist (MicroChem Corp., Newton, Mass.) coated by spinning on the glass substrate. The dried layer with 40 μm thickness was pre-heated at 90° C. for one hour, then exposed to ultraviolet light through a mask having the three sets of channel networks 8A, 8B and 8C (as illustrated in the exemplary embodiment of FIG. 3) with 150 μm width, followed by hardening the exposed portion by curing at 90° C. for one hour. The photoresist was developed with PGMEA (propylene glycol monomethyl ether acetate), the uncured portion is removed with water. The cured portion was dried to form an embossed SU-8 layer on the glass substrate (embossed glass substrate). This embossed portion was used as a mould for forming the immobilization layer of the enzyme immobilization channel.

The pattern of the evaporated gold layers was formed to correspond to the reaction network channel path of the final fabricated microfluidic device. Moreover, the three sets of the network sections of evaporated gold layer 8A, 8B and 8C are immobilized with various enzymes as described in the following EXAMPLES. In this exemplary embodiment, an electrode made from platinum 7 is formed on the substrate at the time of the pre-treatment to analyze a desired component of a solution. Those of skill in the art will appreciate that the sensor can be mounted to the substrate at any convenient time.

Example 2

Fabrication of the Immobilization Layer

As described above, surface treatment of the substrate results in an SU-embossed glass substrate. This embossed portion was used as a mould for forming the immobilization layer of the enzyme immobilization channel.

The PDMS (polydimethyl siloxane) layer with three sets of network portions was obtained by pouring a solution having a mixture of 10 parts of PDMS (polydimethyl siloxane) solution (Sylguard™ 184, Dow Corning Corp.) and 1 part of hardening compound onto the embossed glass substrate mould described in Example 1 to a thickness 1-2 mm. The air was evacuated using a vacuum system and the PDMS layer allowed to harden for one hour at 70° C. The hardened film was then gradually removed from the embossed glass substrate. The cured PDMS layer having a total thickness of about 230 μm then forms a image of the embossed substrate. The channel networks 12A, 12B and 12C had a height or diameter of approximately and 30-40 μm channel and a width 12D about the same or slightly larger than the width of the embossed substrate used as the mould.

Apertures were opened at each inlet 13 and outlet 14 of the three fabricated immobilization channel networks 12A, 12B and 12C. The obtained immobilization layer 11 was attached on the glass substrate such that the pre-treatment channel networks 8A, 8B and 8C having the evaporated gold layer aligns with the immobilization channel networks 12A, 12B and 12C thereby forming closed channels. To facilitate an accurate position alignment, the alignment markers 15 were prepared on the glass substrate 10 and the embossed glass substrate 10. As will be recognized by those of skill in the art, use of the alignment markers on the embossed glass substrate aids in the ease of copying and forming the replica of the PDMS layer.

Example 3

Immobilization of the Enzyme

After attaching the immobilization layer for the enzyme immobilization, each of the different enzyme solutions was injected at the aperture of the inlet of each channel network 12A, 12B, 12C in the order desired. The pressure at the outlet was reduced by applying a vacuum or using a syringe (for example) or aspirator to introduce the enzyme solution to the channel providing enzyme immobilization on the evaporated gold layer. In addition, by reducing the pressure, the grooved PDMS (polydimethyl siloxane) immobilization layer 11 has greater adherence to the glass substrate, preventing a leak of enzyme solution from the channel, and allowing better solution flow in the channel. Thus, in one exemplary embodiment, invertase solution was allowed to flow into channel the first channel 12A, mutarotase solution was flowed into the second channel, 12B and glucose oxidase solution was flowed into the third channel 12C allowing each enzyme to be immobilized on the evaporated gold layer. In this embodiment, the concentration of each enzyme is approximately 3 mol/l. However, it should be appreciated that for different cognitive agents, different substrates or different assays, etc. different concentrations of cognitive agents may be desirable. Following cognitive agent immobilization, the grooved PDMS (polydimethyl siloxane) layer is removed from the glass substrate. The substrate is then washed with distilled water to remove excess enzyme to provide the enzyme immobilized (cognitive agent) substrate.

Fabrication of the Microfluidic Device

Example 4

Fabrication of the Reaction Channel Layer

A glass substrate with an embossed portion is prepared by the same method described in Examples 1 and 2 to form a reaction channel layer having corresponding network sections as the pre-treatment and immobilization layers. In this exemplary embodiment the reaction layer is formed of PDMS (polydimethyl siloxane). This channel bearing layer becomes the reaction layer. The reaction channel, is formed using the embossed mould as described in Examples 1 and 2. In this particular Example, the dimension of the reaction channel is 250 μm width and 70 μm depth (height) although those of skill in the art will recognize that the dimensions can be optimized for each desired use. As illustrated in FIGS. 1 and 4, the difference between the reaction layer and the immobilization layer used for enzyme immobilization is the reaction layer provides a continuous channel connecting all of the reaction networks sections 4A, 4B and 4C as shown in FIG. 1.

Following the opening of an aperture at the inlet and outlet of the reaction layer channel 4, the reaction layer 3 was attached onto the glass substrate by aligning each of the position markers on the reaction layer and the substrate. This forms the microfluidic device. As with the immobilization layer, alignment markers were formed on the grooved layer, and then the alignment markers were used to align the immobilized enzyme substrate with the reaction layer.

Example 5

Sucrose Concentration Measurement

The microfluidic device of this invention was used to measure the sucrose concentration in sugar cane. The procedure starts from using squeezed sugar cane juice as a solution sample; dropping the solution sample (about 2-5 µl/drop) in the inlet of the microfluidic device where the solution sample flows into the channel by reducing the outlet pressure. An amount of hydrogen peroxide as a final reaction product was measured using a hydrogen peroxide sensitive electrode and thereby determining the sucrose concentration in the sugar cane.

While this invention has been described in conjunction with the various exemplary embodiments outlined above, various alternatives, modifications, variations, improvements and/or substantial equivalents, whether known or that are or may be presently unforeseen, may become apparent to those having at least ordinary skill in the art. accordingly, the exemplary embodiments according to this invention, as set forth above, are intended to be illustrative not limiting. various changes may be made without departing from the spirit and scope of the invention. therefore, the invention is intended to embrace all known or later-developed alternatives, modifications, variations, improvements and/or substantial equivalents of these exemplary embodiments.

What is claimed is:

1. A method of fabricating a microfluidic device comprising the steps of:
   providing a substrate;
   attaching an immobilization layer having one or more channel networks formed therein to the substrate;
   flowing one or more solutions of cognitive agents into the one or more channel networks;
   immobilizing the one or more cognitive agents onto the substrate surface at the one or more channel networks;
   detaching the immobilization layer from the substrate; and
   attaching a reaction layer comprising a single reaction channel to the substrate wherein the single reaction channel is aligned with the one or more channel networks.

2. The method of fabricating the microfluidic device of claim 1, wherein each of the one or more solutions of cognitive agents comprises an enzyme, an antigen, an antibody, a protein, a receptor, a nucleic acid or a combination thereof.

3. The method of fabricating the microfluidic device of claim 1, further comprising a step of pre-treating the substrate surface prior to the step of attaching the immobilization layer.

4. The method of forming the microfluidic device of claim 3 wherein the pre-treating is performed prior to flowing the cognitive through the channel network.

5. The method of claim 3 wherein the pre-treating comprises depositing a gold layer.

6. The method of fabricating the microfluidic device of claim 3 wherein the pre-treating is performed simultaneously with forming a sensor on the substrate surface.

7. The method of fabricating the microfluidic device of claim 1 further comprising the step of forming a first alignment marker on the substrate and a second alignment marker in the immobilization layer, the first and second alignment marker positioned to facilitate alignment of the immobilization layer with the substrate during the attaching of the immobilization layer to the substrate.

8. The method of fabricating the microfluidic device of claim 4 further comprising forming a third alignment marker on the reaction layer, the third alignment marker positioned to facilitate alignment of the reaction layer with the substrate during the attaching of the reaction layer to the substrate.

9. The method of fabricating the microfluidic device of claim 1 wherein the steps are carried out in the order recited.

10. The method of fabricating the microfluidic device of claim 1 wherein one or more solutions of cognitive agents is flowed in a discrete channel network.

11. The method of fabricating the microfluidic device of claim 1 wherein the one or more channel networks are discrete channel networks and each of the one or more cognitive agents is immobilized in a discrete channel network.

* * * * *

UNITED STATES PATENT AND TRADEMARK OFFICE
CERTIFICATE OF CORRECTION

PATENT NO. : 9,452,428 B2
APPLICATION NO. : 14/534502
DATED : September 27, 2016
INVENTOR(S) : Sriyudthsak et al.

Page 1 of 1

It is certified that error appears in the above-identified patent and that said Letters Patent is hereby corrected as shown below:

At Column 16, Line 26 (Claim 8, Line 2):
"claim 4 further"

should read:
--claim 7 further--

Signed and Sealed this
Twenty-first Day of February, 2017

Michelle K. Lee
*Director of the United States Patent and Trademark Office*